United States Patent
Buchanan

(10) Patent No.: US 7,762,118 B2
(45) Date of Patent: Jul. 27, 2010

(54) AUTO-POSITIONING ULTRASONIC TRANSDUCER SYSTEM

(75) Inventor: Randy K. Buchanan, Hattiesburg, MS (US)

(73) Assignee: The University of Southern Mississippi, Hattiesburg, MS (US)

( * ) Notice: Subject to any disclaimer, the term of this patent is extended or adjusted under 35 U.S.C. 154(b) by 568 days.

(21) Appl. No.: 11/800,424

(22) Filed: May 4, 2007

(65) Prior Publication Data

US 2008/0022776 A1 Jan. 31, 2008

Related U.S. Application Data

(60) Provisional application No. 60/798,364, filed on May 5, 2006.

(51) Int. Cl.
*G01F 25/00* (2006.01)
(52) U.S. Cl. .......................................... 73/1.16
(58) Field of Classification Search .................. None
See application file for complete search history.

(56) References Cited

U.S. PATENT DOCUMENTS

| | | | |
|---|---|---|---|
| 4,227,407 A | | 10/1980 | Drost |
| 4,586,379 A | * | 5/1986 | Burkhardt, Jr. ............... 73/622 |
| 5,179,862 A | * | 1/1993 | Lynnworth ............... 73/861.28 |
| RE36,130 E | * | 3/1999 | Haynes ........................ 73/622 |
| 6,047,602 A | | 4/2000 | Lynnworth |
| 6,626,049 B1 | | 9/2003 | Ao |
| 7,096,135 B2 | | 8/2006 | Ao et al. |
| 2003/0172735 A1 | * | 9/2003 | Lam et al. ..................... 73/622 |
| 2004/0020297 A1 | * | 2/2004 | Ziola et al. .................... 73/634 |

OTHER PUBLICATIONS

"Nondestructive Testing Encyclopedia," by Rolf Diederichs, *The e-Journal of Nondestructive Testing*, retrieved May 25, 2004 from www.ndt.net/article/az/ut_idx.htm.
"PXI and Compact PCT," *National Instruments*, retrieved Feb. 12, 2005 from www.ni.com/pxi.
"Internet.Com Small Business Computing Channel," "Webopedia," retrieved Feb. 12, 1005 from www.webopedia.com/TERM/P.PCI.

* cited by examiner

*Primary Examiner*—Robert R Raevis
(74) *Attorney, Agent, or Firm*—Howrey LLP

(57) ABSTRACT

An ultrasonic transducer apparatus and process for determining the optimal transducer position for flow measurement along a conduit outer surface. The apparatus includes a transmitting transducer for transmitting an ultrasonic signal, said transducer affixed to a conduit outer surface; a guide rail attached to a receiving transducer for guiding movement of a receiving transducer along the conduit outer surface, wherein the receiving transducer receives an ultrasonic signal from the transmitting transducer and sends a signal to a data acquisition system; and a motor for moving the receiving transducer along the guide rail, wherein the motor is controlled by a controller. The method includes affixing a transmitting transducer to an outer surface of a conduit; moving a receiving transducer on the conduit outer surface, wherein the receiving transducer is moved along a guide rail by a motor; transmitting an ultrasonic signal from the transmitting transducer that is received by the receiving transducer; communicating the signal received by the receiving transducer to a data acquisition and control system; and repeating the moving, transmitting, and communicating along a length of the conduit.

20 Claims, 1 Drawing Sheet

AUTO-POSITIONING ULTRASONIC TRANSDUCER SYSTEM

The present application claims priority to U.S. Provisional Patent Application Ser. No. 60/798,364 filed May 5, 2006, the entire contents of which are incorporated herein by reference.

FEDERALLY SPONSORED RESEARCH

The United States government may own rights in the present invention pursuant to University of Southern Mississippi subcontract No. 02-10-032 to support NASA grant No. NCC5-574 under the Mississippi NASA EPSCoR program.

FIELD OF THE INVENTION

The present invention generally relates to flow measurement. In particular, the present invention relates to an apparatus and method for automatically adjusting the placement of the transducers of an ultrasonic flow measurement system.

BACKGROUND OF THE INVENTION

There is a need for improved measurement of cryogenic flows of varying fluids, temperatures, flow rates, and pipe diameters in a noninvasive manner. Specifically, instrumentation that may used in rocket engine test areas is needed. Commercially available flowmeters lack low temperature capabilities. Ultrasonic instrumentation is a potential alternative for traditional cryogenic flow measurement because of its noninvasive nature. Optimization of positioning ultrasonic transducers would greatly increase the versatility of cryogenics instrumentation.

An acoustical or ultrasonic wave is subject to the mediums it must traverse. Interfaces between dissimilar materials within the ultrasonic signal path of flow instrumentation cause an ultrasonic wave to be subjected to attenuation, reflection, and refraction. The consequences of these effects may be minimized through improved design and development of ultrasonic instrumentation. Within an ultrasonic flow measurement tool there are many interfaces that the ultrasonic wave must traverse. In practice, the connection of ultrasonic transducers to the exterior of pipe typically complicates the interface issue and results in appreciable setup and calibration time.

Initially, fundamental research included the transit methods of measurement for industrial applications. Early research revealed the underlying equations used to calculate transit times in isotropic materials in different modes of propagation. However, as the technology matured, later work expanded to new industrial applications and improved ultrasonic instrumentation. Unfortunately, later work publications did not provide details because of competitive pressures.

Ultrasonic flow measurement technology monitors a generated signal between a transmitter and a receiver to determine the location of the signal within an object, such as a pipe. Conventional ultrasonic technology uses software to calculate the predicted location of a signal received from an ultrasonic transmitter. The calculations involve variables that may be mere estimates and excludes some variables that may be considered negligible.

Most modern ultrasonic flow instrumentation requires calculated transducer positioning and manual setup. The signal path of the instrumentation is altered by pipe and fluid properties including impedance, reflection, refraction, diffraction and scattering, absorption, and multiple boundary interfaces. Only by identifying the location of the optimum waveform can the combination effects of all these variables be accurately determined.

The current methods for predicting signal location may not be acceptable in applications requiring a more exact determination of flow. Thus, a system for measuring a received signal directly, after all effects of system variables have had influence on the signal, and automatically determining the optimal position for the receiving transducer is needed.

The aerospace testing industry would benefit from an improvement in ultrasonic flow instrumentation. The industry requires instrumentation with low temperature capabilities that can measure cryogenic flows in a noninvasive manner in field applications with varying fluids, temperatures, flow rates, and pipe diameters. An ultrasonic system that automatically determines the optimal receiving transducer position while accounting for the various system effects is desirable. Developing ultrasonic instrumentation in combination with computational fluid dynamics software is also desirable.

BRIEF SUMMARY OF THE INVENTION

An ultrasonic transducer apparatus and process for determining the optimal transducer position for flow measurement along a conduit outer surface is provided. The apparatus includes a transmitting transducer for transmitting an ultrasonic signal, said transducer affixed to a conduit outer surface; a guide rail attached to a receiving transducer for guiding movement of a receiving transducer along the conduit outer surface, wherein the receiving transducer receives an ultrasonic signal from the transmitting transducer and sends a signal to a data acquisition system; and a motor for moving the receiving transducer along the guide rail, wherein the motor is controlled by a controller. The method includes affixing a transmitting transducer to an outer surface of a conduit; moving a receiving transducer on the conduit outer surface, wherein the receiving transducer is moved along a guide rail by a motor; transmitting an ultrasonic signal from the transmitting transducer that is received by the receiving transducer; communicating the signal received by the receiving transducer to a data acquisition and control system; and repeating the moving, transmitting, and communicating along a length of the conduit.

BRIEF DESCRIPTION OF THE DRAWINGS

Features of the present invention as well as a preferred mode of use, further objectives, and advantages thereof, will best be understood by reference to the following detailed description of an illustrative embodiment when read in conjunction with the accompanying drawings, wherein.

DETAILED DESCRIPTION OF THE INVENTION

Figure 1:
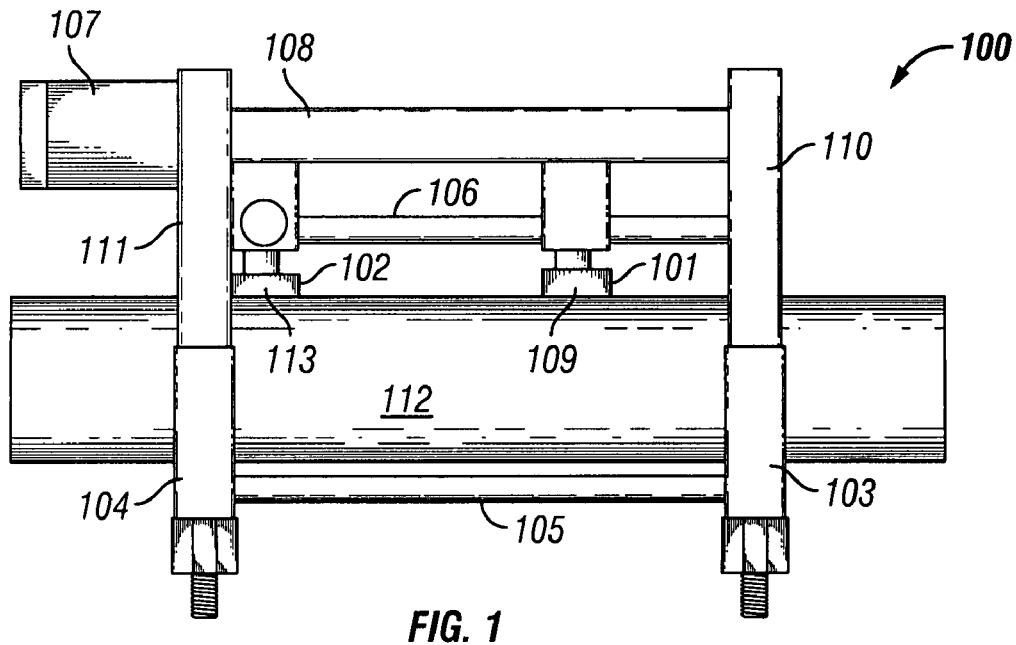
FIG. 1 is a schematic diagram of an embodiment of the auto-positioning ultrasonic transducer apparatus attached to a pipe.

The present invention provides an auto-positioning ultrasonic transducer that automatically adjusts the positioning of at least one transducer in an ultrasonic measurement system. A positioning system was developed for the purpose of minimizing setup time and increasing accuracy with experimentally driven transducer placement data. The positioning system analyzes the signal available to a receiver and verifies that the transducers are placed in locations that provide optimum reception. This is accomplished with minimum system effects from the conduit and fluid.

The auto-positioning ultrasonic transducer system includes a fixed transmitting transducer, movable receiving transducer, guide rail, motor, encoder, and a computer data acquisition and control system. A guide rail is also included, along which a receiving transducer is moved along an outer surface of the conduit while maintaining continuous contact with the outer surface as the receiving transducer receives an ultrasonic signal from the fixed transmitting transducer.

A motor and encoder allow for moving the receiving transducer along the outer surface of the conduit and determining the location of the receiving transducer, respectively. Additionally, a software program can be used to track the steps of the motor for determining the location of the receiving transducer. An ultrasonic flowmeter that provides excitation signals for the transmitting transducer and processing of signals from the receiving transducer may also be used.

Further, a programmable data acquisition and control system with digital and analog inputs/outputs for collecting output signal strength from transmitting and receiving transducers may be utilized. The data acquisition system creates a signal strength data file and allows for the searching of the data file for an optimized user-defined parameter. A data file is created from the collected signals by the data acquisition system, which also allows the data file to be searched for a specific parameter high or low signal. The optimal location is then calculated based on the specific value signal and the motor is directed by the instructions given by the control system to move the receiving transducer to the optimal location. The control system directs the motor to move the receiving transducer to the desired location along the conduit. The data acquisition and control system comprises a user interface program for parameter input. This method may use a wave amplitude as the user specified parameter to be searched.

Both the transmitting transducer and the receiving transducer can be made of a piezo electric material. The receiving transducer is moved linearly along the conduit and in the same axis as that of the transmitting transducer. Alternatively, the receiving transducer is moved linearly along the conduit and in an axis parallel to that of the transmitting transducer. In addition, an encoder can be located with the motor or remotely from the motor.

A shock absorber system allows the receiving transducer to make continuous contact with the conduit while concurrently allowing movement of the receiving transducer along the conduit.

A noninvasive measurement apparatus with a transceiver to traverse a specified axial length of the pipe section while transmitting and receiving the acoustical signal to determine the optimum transducer location is provided. The transducer will be moved along the pipe and set by a stepper motor driven by a linear table with a controller. The operator sets up operational parameters through a user interface. Once the user initiates the auto-positioning action, the transducer scans the predetermined length of the pipe and the data acquisition system records the received signal to a file. Once the initial scan is completed and based on programmed instructions, the user interface program then calculates the optimum location and directs the motor to move the movable transducer to the desired location. Thus, the system measures the received signal directly, after all effects of system variables have had an influence on the signal.

Two principal traversal methods are available for measuring flow in a pipe with ultrasonic signals. One method involves sending the signal from one side of the pipe to the other and the alternate method bounces the signal off the interior pipe wall one or more times. Generally, the bounce method is preferred for anything other than very large pipes, because of its higher degree of accuracy and lesser difficulty of installation. Only in cases of poor interior pipe surfaces or highly attenuating fluids is the direct method preferred. When the transducers are inserted permanently into the pipe they are called "wetted transducers." However, if the transducers are clamped to the exterior of the pipe, they are called "non-wetted." It is the non-wetted method that is of interest because it has the most utility in non-permanent testing and flow validation applications.

Methods of attaching the transducers to the pipe vary and generally consist of some or all of an arrangement of chains, bands, clamps, bolts, hooks, and adjustment devices. The size of the clamping fixture is dictated by the diameter of the pipe in which flow is being measured. The final goal of installation is effective contact between the ultrasonic transducers and contact with the pipe at a predetermined distance and geometrically situated appropriately with all intended axes.

There are several variables that affect the transmission, propagation, and reception of the acoustical wave used in the flow measurement system. These variables include but are not limited to impedance, reflection, refraction, pipe density, fluid density, fluid homogeneity, temperature, angle of incidence, and transducer planar alignment in all axes.

Angle of Incidence

Alignment of the ultrasonic transducers is calculated for longitudinal one dimensional spacing only and assumes other axes are properly aligned. In addition to the longitudinal spacing, the transducers axes must be aligned in other dimensions before the acoustical wave can be transmitted in the anticipated fashion. These assumed alignments include pitch, yaw, and roll.

Severe variance in any of these axes could produce effects as indicated in Tables 1 and 2. A significant change in signal location could mean that the receiver would not be placed in the ideal location for receiving the transmitted signal and therefore be subject to noise and reflected signals. A change in acoustical wave plane orientation would cause changes in reflection and refraction angles, thus affecting the location for optimum receiver positioning. Yaw variations over ±18° resulted in as much as 26 percent signal attenuation. Roll variations of ±30° resulted in as much as 42 percent signal attenuation from the normal. Pitch variations were more difficult to implement. When the pitch was varied, acoustical coupling was lost and essentially no signal appeared at the receiver.

TABLE 1

Roll Measurements from Transducer Positioning Testing

| ANGLE | DESCRIPTION | PLANE | VARIANCE | RESULT |
|---|---|---|---|---|
| θ | Pitch | YZ | Rotate up or down | Change in received signal location |
| φ | Yaw | XY | Rotate left or right | Change in acoustical wave plane orientation |
| α | Roll | XZ | Tilt left or right | Change in acoustical wave plane orientation |

Yaw Measurements

| Δx | φ° | Transmitted Vpk-pk | Received mVpk-pk |
|---|---|---|---|
| 60 mm | 18 | 130 | 244 |
| 60 mm | 15 | 130 | 258 |

TABLE 1-continued

| Δx | | | |
|---|---|---|---|
| 60 mm | 10 | 130 | 302 |
| 60 mm | 5 | 130 | 297 |
| 60 mm | 0 | 130 | 309 |
| 60 mm | −5 | 130 | 300 |
| 60 mm | −10 | 130 | 295 |
| 60 mm | −15 | 130 | 243 |
| 60 mm | −18 | 130 | 228 |

Roll Measurements

| Δx | α° | φ° | Transmitted Vpk-pk | Received mVpk-pk |
|---|---|---|---|---|
| 60 mm | 30 | 0 | 130 | 214 |
| 60 mm | 20 | 0 | 130 | 194 |
| 60 mm | 10 | 0 | 130 | 216 |
| 60 mm | 0 | 0 | 130 | 309 |
| 60 mm | −10 | 0 | 130 | 234 |
| 60 mm | −20 | 0 | 130 | 202 |
| 60 mm | −30 | 0 | 130 | 180 |

Pitch Measurements: Pitch deviation causes loss of signal.

TABLE 2

Yaw Measurements from Transducer Positioning Testing
Yaw Measurements

| Δx | φ° | Transmitted Vpk-pk | Received mVpk-pk |
|---|---|---|---|
| 60 mm | 18 | 130 | 244 |
| 60 mm | 15 | 130 | 258 |
| 60 mm | 10 | 130 | 302 |
| 60 mm | 5 | 130 | 297 |
| 60 mm | 0 | 130 | 309 |
| 60 mm | −5 | 130 | 300 |
| 60 mm | −10 | 130 | 295 |
| 60 mm | −15 | 130 | 243 |
| 60 mm | −18 | 130 | 228 |

TABLE 3

Roll Measurements from Transducer Positioning Testing
Roll Measurements

| Δx | α° | φ° | Transmitted Vpk-pk | Received mVpk-pk |
|---|---|---|---|---|
| 60 mm | 30 | 0 | 130 | 214 |
| 60 mm | 20 | 0 | 130 | 194 |
| 60 mm | 10 | 0 | 130 | 216 |
| 60 mm | 0 | 0 | 130 | 309 |
| 60 mm | −10 | 0 | 130 | 234 |
| 60 mm | −20 | 0 | 130 | 202 |
| 60 mm | −30 | 0 | 130 | 180 |

Pitch measurements also show how pitch deviation causes a loss of signal. The acoustic impedance of any medium is the opposition to displacement.

Impedance

The acoustic impedance of any medium is the opposition to displacement of its particles by an acoustical wave. The impedance of a conducting medium is considered to be the combined effect of the pipe and the fluid transported within. The composition of the pipe and fluid determine their overall ability to transfer acoustic energy. The property of resisting the transfer of the wave front pressure is expressed in terms of acoustic pressure, and is the product of the density and the wave velocity. Acoustic impedance may be expressed in units of Rayls, in which one Rayl is one kilogram per second times meter squared. For example, the acoustic impedance of water is 1.49 MRayls. When sound strikes an acoustic interface, some amount of sound energy is transmitted across the boundary and some amount is reflected.

Reflection and Refraction

When using the double traverse method, the signal of interest is a reflected wave. Variations in properties at interfaces and within mediums along the wave path affect the location of the reflected wave. The reflected energy is the square of the difference divided by the sum of the acoustic impedances of the two materials. The impedance of the respective materials that compose the differing boundaries affects the ability of transmission, as well as the reflection effects between two boundaries. A wave front traveling at a particular velocity determined by the acoustic impedance of the material undergoes a change in velocity magnitude and direction when suddenly entering another material that has a different level of acoustic impedance. The greater the difference in the acoustic impedances of the two materials, the greater the amount the ultrasonic signal is refracted. Shear waves are not refracted as much as longitudinal waves, because they travel at a lesser velocity. A multitude of reflected and refracted waves eventually reach the receiver at varying times through the measurement process due to varying propagation travel times. These signals could affect the measurement reading by overriding or biasing the intended wave if the receiver is not located in the optimum location.

Densities and Fluid Properties

Properties of the fluid that are assumed to be known are the composition, density, viscosity, temperature, and fluid homogeneity. In normal applications, pipe and fluid density are assumed. These conditions are entered into the setup of the flow meter as constant values, as well as pipe thickness, pipe diameter, and other variables. Variations from these "known" values, other materials along the wave propagation path, and effects of multiple boundary interfaces are not considered. An ultrasonic transducer system has varieties of material boundary interfaces that present impedance mismatches for the propagating ultrasonic wave. For example, an interface boundary exists between the transmitter transducer surface and the exterior surface of the pipe, which may or may not include a coupling agent. There may also be air pockets between the two dissimilar materials. Materials of differing density accordingly exhibit differing acoustical velocities. A standard two transducer arrangement can present eight or more intrinsic boundary transfers that result in variations of sound wave velocity and propagation angles in addition to signal attenuation due to diffraction, scattering, and absorption.

The composition of a fluid is often known, and could be a gas or liquid. If the fluid is commonly observed, the characteristics of that fluid may be automatically recalled by the flow meter. The temperature may be considered constant, such as 77° F., or be programmed as a range of process temperatures. The measured fluid is most likely homogeneous and is assumed to have constant density throughout. This assumption neglects the presence of particles, density gradients, and bubbles. The transducer detected wave will be influenced by these factors. Thus, proper positioning in setup becomes even more critical.

The distance traveled (Δx) for the v-bounce method in water with dissimilar transducer and pipe interface using shear wave speeds at 25° C. can be determined using Snell's Law. The relationship may be expressed as $$n_1 \sin \theta_1 = n_2 \sin \theta_2$$

Where $n_1$ and $n_2$ are indices of refraction, and $\theta_1$ and $\theta_2$ are the angles of entry and exit at the boundary of the transducer and pipe. Solving for the refraction angle gives $$\theta_2 = \sin^{-1}\left[\frac{n_1}{n_2}\sin\theta_1\right] = 58.75°$$

using shear velocities. In this case, the distance $\Delta x_1=3.913$ mm (tan 58.75°) or 6.447 mm. For the pipe to water interface, $$\theta_2 = \sin^{-1}\left[\frac{n_1}{n_2}\sin\theta_1\right] = 24.53°$$

using shear velocities. In this case, the distance $\Delta x_2=52.501$ mm (tan 24.53°) or 23.96 mm. The solution for the total distance would then be the (3.913 mm+23.96 mm) multiplied by 2 in consideration of the double traverse. Total distance would effectively equal a calculated value of 60.820 mm or 2.395 inches.

The auto-positioning ultrasonic transducer system includes a fixed transmitting transducer, movable receiving transducer, motor, encoder, and a computer data acquisition and control system. A guide rail is also included along which a receiving transducer is moved along an outer surface of the conduit while maintaining continuous contact with the outer surface as the receiving transducer receives an ultrasonic signal from the fixed transmitting transducer.

The auto-positioning system 100 was fabricated from a combination of transducer mounting brackets 101, 102 and other components designed specifically for this application, as shown in FIG. 1. The mounting components mounted on a pipe 112 consisted of pipe mounting clamps 103, 104 and guide rods 105, 106. Designed and fabricated components included the motor and encoder 107, and positioner assembly 108, as well as the traversing transceiver arrangement 109, fixed transceiver 113, and the positioner mounting brackets 110, 111. The motor 107 and related components were attached to the positioner mounting bracket 111, which was machined from metal stock.

Figure 2:
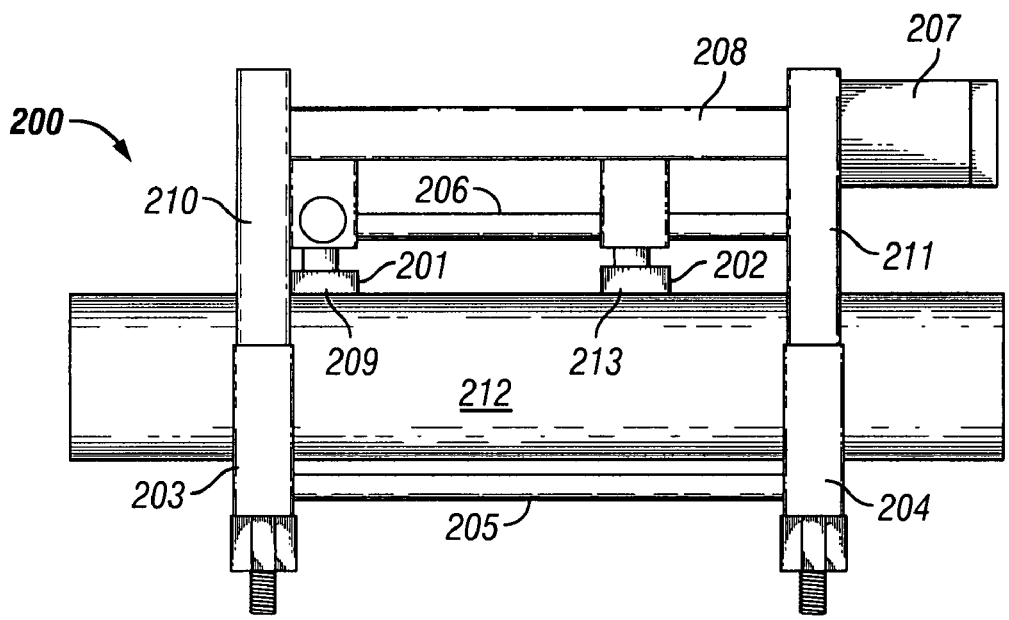
FIG. 2 is a schematic diagram of an additional embodiment of the auto-positioning ultrasonic transducer apparatus attached to a pipe.

Similarly, FIG. 2 provides an additional embodiment of an auto positioning system 200. Pipe 212 is connected to transducer mounting brackets 201, 202 and to pipe mounting clamps 203, 204. Guide rods 205, 206 are also mounting components. The motor and encoder 207 is configured to move along the positioner assembly 208 in a direction opposite the movement of the embodiment illustrated by FIG. 1. That is, the transversing transceiver arrangement 209 and fixed transceiver 213 provide motion in the opposite direction of the embodiment of FIG. 1. The positioner mounting brackets 210, 211 support the motor 207 and transceivers 209, 213.

A motor and encoder are selected to allow for moving the receiving transducer along the outer surface of the conduit and for determining the location of the receiving transducer, respectively. Alternatively, a software program can be used to track the steps of the motor for determining the location of the receiving transducer. The apparatus also includes an ultrasonic flowmeter that provides excitation signals for the transmitting transducer and processing of signals from the receiving transducer.

The ultrasonic flowmeter requires that the downstream transducer be spaced a distance equal to the skip distance from the upstream transducer. This positioning of the downstream transducer places it downstream from the point where the sound wave is reflected off the back wall of the pipe and at the point where the reflected wave intersects the front wall of the pipe. Since this location places the transducer in the area with the greatest intensity, it is believed that at this location the piezo electric material in the transducer will be under the greatest stress and will therefore generate the optimum signal.

The apparatus uses a programmable data acquisition and control system with digital and analog inputs and outputs for collecting output signal strength from transmitting and receiving transducers. The data acquisition system creates a signal strength data file and allows for the searching of the data file for a user-defined parameter having the highest or lowest value. The data acquisition and control system comprises a user interface program for parameter input.

A data file is created from the collected signals by the data acquisition system, which also allows the data file to be searched for the signal with the highest value of the parameter specified by the user. The optimal location is then calculated based on the highest value signal and the motor is directed by the instructions given by the control system to move the receiving transducer to the optimal location. Note that this method may use a wave amplitude as the user specified parameter to be searched. The control system directs the motor to move the receiving transducer to the desired location along the conduit.

The auto-positioning system was composed of the following major components:

Ultrasonic transducers (allow transmission and reception of ultrasonic signal)

Controller with appropriate programming and analog and digital inputs/outputs (I/O) (provides acquisition of data and controlling signals per programming)

Stepper motor with linear table (moves transducer down the pipe in a linear fashion)

Conventional ultrasonic flowmeter (provides excitation signal for transmission transducer and processing of signal from receiving transducer)

Mounting bracket to fit configuration (allows auto-positioning system to be fitted to pipe)

Shock absorber system (allows transducer to make acoustical contact with the pipe while concurrently allowing movement along the pipe)

Appropriate power supplies.

Both the transmitting transducer and the receiving transducer can be made from a piezoelectric material. The receiving transducer is moved linearly along the conduit and in the same axis as that of the transmitting transducer. Alternatively, the receiving transducer is moved linearly along the conduit and in an axis parallel to that of the transmitting transducer. In addition, the encoder can be located with the motor or remotely from the motor. A shock absorber system allows the receiving transducer to make continuous contact with the conduit while concurrently allowing movement of the receiving transducer along the conduit.

Two flow meters were examined to illustrate standard setup procedures used in off-the-shelf flow measurement instruments. In this case, a panel flow meter and a portable flow meter user setup and transducer placement calculations were compared. The transducer distance calculation results of the flow meters were compared to analytical calculations and the positioning system data.

TABLE 3

Flow Meter Setup Parameters

| PARAMETER | VALUE | UNITS |
|---|---|---|
| Transducer number | 21 | N/A |
| Wedge type - Rayleigh or Shear Wave | shear | N/A |
| Frequency of special transducer | 1 | MHz |
| Time window | 176 | μs |
| Wedge angle | 60 | degrees |
| Wedge sound speed | 10133.8 | Ft/s |
| Pipe material | steel | stainless |
| Pipe OD or circumference | 2.375 | inches |
| Pipe wall thickness | 0.154 | inches |
| Clamp-on only: | | |
| Pipe lining material | 1-7† | N/A |
| Pipe lining thickness | 0.2 | inches |
| Fluid type | water | N/A |
| Energy option | On/Off | N/A |
| Reynolds correction | On | N/A |
| Kinematic viscosity of fluid | 10.76E−6 | Ft^2/s |
| Flow calibration factor | 1 | N/A |
| Depth of reflector | N/A | N/A |
| Number of traverses | 2 | N/A |

A development fixture was created to provide a means for creating an auto-positioning system comparison working prototype. The test configuration consisted of a 21-inch length of 2" stainless steel pipe section capped at both ends. The pipe was filled with water to provide proper acoustical impedance comparable to water based dynamic testing. The applicable sound speeds were determined for 316 stainless steel to be 10,105 ft/s and 4862 ft/s for water.

Development occurred in two major phases. The initial manual positioning phase utilized hardware for mounting the movable and fixed transducer to the pipe, and required manual positioning and signal measurement. Once the initial manual positioning phase had been finalized, a computer based data acquisition and control system was developed that automatically operated the system when activated.

Tests were conducted to verify that a simple continuous square wave would have maximum amplitude upon reception at a predetermined location. For the initial test, the transducers were setup in a double-reflection Z-type configuration on the same stainless steel pipe that was used in previous tests, with all the pipe parameters remaining consistent. The flow meter software calculated the axial spacing of the transducers to be 3.72 cm (1.46 in). The transmitting transducer was attached to a signal generator that was again set up for a 10 volt peak-to-peak square wave with a frequency of 1.2 MHz. The receiving transducer was attached to the oscilloscope by means of ultrasonic VHF cables. The transducers were then placed directly across from one another and moved manually along the axis of the pipe in increments of 0.5 cm (0.197 in).

Note that the controller and user interface could have been implemented with different hardware or software and achieved similar results. These parameters were selected to implement the auto-positioning concept. A plot of signal amplitude as a function of propagation distance shows that the signal amplitude is at a maximum at about 2.20 inches and is at a minimum at about 1.95 inches and 2.80 inches.

Another goal of the system design was to determine transducer spacing and reduce the amount of system parameter programming required by commercial flow meters. Therefore, it was necessary to examine the signals produced by the transducers when driven by commercial flow meters, so that effects on these signals could be understood. It was necessary to examine these signals at the source as well as after traversing multiple boundary layers with varying acoustical velocities. It was also deemed necessary to identify any unique properties associated with the transmitted signal. If unique characteristics of the signal could be identified, the characteristics could be used to determine the proper transducer spacing while disregarding many of the system variables, thus eliminating the need to know, locate, or calculate many of the process parameters. The signal voltage amplitude is an example of an identifiable characteristic that could be used to determine appropriate transducer location for proof-of-concept purposes.

To minimize errors related to transducer setup and unknown variables, a calibration system was developed to automatically verify acoustical waveform properties for the purpose of proper transducer positioning. The system was designed with a two-transducer double traverse arrangement. Transducers normally used in manual setup for flow measurement were configured to fit a self-contained transducer positioning assembly. Control and data acquisition were provided by test bench instrumentation including a complete National Instruments PXI virtual instrumentation station. The PXI chassis was equipped with analogue and digital data acquisition, digital multimeter, arbitrary waveform generator, image acquisition, and a multi-channel oscilloscope. All measurements for the test bench were performed through the station hardware interface and processed through a virtual instrumentation software interface. Receiver transducer output signals were connected to the input of the test station to provide insight into the signal characteristics and for purposes of signal conditioning and analysis.

The auto-positioning test bench includes a National Instruments PXI-1000B computer system, Agilent oscilloscope, Hewlett-Packard multimeter, and other basic test instruments. Components of this test configuration include the following:

Agilent E4402B ESA-E spectrum analyzer
Agilent 54621A oscilloscope
Hewlett-Packard 34401A Digital Multimeter
Hewlett-Packard E3631A triple output power supply
BK Precision Triple Output DC Power Supply
National InstrumentsPXI 1000-B computer system
Ealing 62-1938 2'×3' aluminum plate breadboard base
Various Positioning Hardware.

The positioning system test bench makes use of LabVIEW interface to control the system's behavior. Analog signals are transferred to the PXI station which provides the necessary user interface. When the PXI receives a transducer output signal, the LabVIEW program analyzes signal characteristics, such as amplitude and stores the data to a file. Tracking of stepping counts, as with an encoder, is used in conjunction with a discrete module driver to record this position. The test station allows for full traversal of the pipe within the test fixture and the subsequent recording of all acquired data.

Commercially available transducers were used to analyze the accuracy of off-the-shelf flowmeter software, analytical calculations, and the positioning system. The output of the transducers used consisted of ultrasonic waves with well defined characteristic peaks in the form of a time domain pulses with 5 to 7 half-cycles with varying duty cycling.

An axial spacing of 3.72 cm (1.46 in) corresponds to 5 cm on a plot of voltage (positioning signal amplitude) as a function of distance (position on a pipe) due to a difference in the measurement reference points. From the results, it can be concluded that there is a local maxima were the flow meter determined the transducer should be placed. This position of around 5 to 5.5 cm (1.97 to 2.2 in) bears some close proximity with analytical calculations of 6.35 cm (2.5 in). The limitations of the manual test configuration were known, and, therefore, considered to be a limiting factor in terms of signal measurement accuracy. The physical positioning of the transducer had some effect on the signal strength.

A signal measured at the receiving transducer was captured and analyzed for various characteristics. Primarily, peak-to-peak voltage was used as a primary evaluation criteria. Proper placement of the transducers is dependent upon the method selected for flow measurement, the operational characteristics of the transducers, the properties of the system, and the application of Snell's law to boundary interfaces that confront the acoustical wave. The receiving transducer was incrementally placed at different positions on the pipe and the resulting waveform captured and recorded. A composite peak value versus position plot was generated. The various waveforms were analyzed for other characteristics that would potentially correlate with the calculated or computed position of optimum position. However, the amplitude analysis ultimately proved a valid indicator of optimum positioning.

The results of the positioning system were compared to the panel flow meter, the portable flow meter, and analytical calculations, as indicated in Table 4. The position calculated by any method had at least 1.2 percent or more error compared to the other methods. The positioning system position was at the most 4.82 percent from the other distance calculations. A maximum error of 4.82 percent, however, translates to a difference in positioning of only 0.145 inches or 3.683 mm. This difference could be an inaccuracy in the system, or conversely, a true representation of the correct position in consideration of all variables in the system.

TABLE 4

Transducer Spacing Comparisons.

| Source | Distance | Mean | Mean Difference | % Error from Mean |
|---|---|---|---|---|
| Panel Flowmeter | 2.421 | 2.366 | 0.055 | 2.346 |
| Portable Flowmeter | 2.396 | 2.366 | 0.031 | 1.289 |
| Analyatical Calculations | 2.395 | 2.366 | 0.030 | 1.247 |
| Positioning System | 2.250 | 2.366 | −0.116 | 4.883 |

| Source | % Error from Panel | % Error from Portable | % Error from Analytical | % Error from System |
|---|---|---|---|---|
| Panel Flowmeter | — | 2.316 | 2.317 | 2.467 |
| Portable Flowmeter | 1.260 | — | 1.273 | 1.356 |
| Analyatical Calculations | 1.219 | 1.231 | — | 1.311 |
| Positioning System | 4.771 | 4.821 | 4.823 | — |

The positioning system was tested on a test fixture to provide automatic transducer positioning and signal measurement on a real pipe configuration. The positioning system uses a virtual instrumentation interface to control the system's behavior. This interface was the only component used in the data acquisition and control process for this configuration.

The stepping was controlled by the by a 500 kS/s, 16-Bit, 8 analog simultaneous sampling input module with pulse generator output. The pulse was a square wave signal with 250 μs high and 250 μs low states. The received analogue transducer signal was transferred to a virtual instrumentation hardware station, and a virtual instrument program stored in the hardware station compared the transferred signal amplitude to the maximum signal amplitude previously sampled. If the signal amplitude was larger than the previously recorded signal amplitude, the present signal position was recorded.

The virtual instrumentation station instructed the controller to step the motor to the next location by generating the proper pulse sequence to step the motor a desired amount. The pulse sequence was fed into the motor driver which increase the voltage in order to meet the voltage specifications for motor operation. The motor then stepped to the next location, provided the limit switch was not activated. Once the limit switch was activated, the positioning system automatically returned to the optimum location saved in memory. The positioning system was mounted to a pipe section to replicate actual industrial application and various tests and analyses were performed.

Tests of repeatability were conducted with the auto-positioning system mounted to the test fixture. The signal amplitude was recorded at 1 mm (0.04 in) increments down the length of the positioning apparatus, approximately 400 mm (15.75 in) in the v-bounce configuration. Other tests conducted focused on section of pipe for the optimum transducer placement location for v-bounce and z-bounce transducer configurations. These tests also scanned in 1 mm (0.04 in) increments, but only in the proximity of the length of pipe around the v and z reflection points. All tests involved scanning the transducer along the required length of the pipe 10 consecutive times with identical testing parameters and procedures.

The auto-positioning system pipe scan data for 10 sequential tests with the transducers set up in a v-bounce configuration was plotted with signal strength in volts as a function of distance in inches. The scan was set for the full length of the positioning assembly to allow analysis of the received signal for the length of potential scan. The auto-positioning system scanned the pipe with the movable transceiver and the received signal was transferred to and recorded by the user interface program.

After investigation, it was determined that the transducer may have not been making optimum contact with the pipe when this data was collected, providing less than desired coupling between the moving transducer and the pipe surface. The plot indicates that the location between the major groups of peaks was between approximately two to five inches. This span of length along the pipe is where the signal peaks of highest levels and durations were measured by the system. Calculated transducer spacing distance was 6.35 cm (2.5 in). It is apparent from the data that the strongest signals are in the proximity of this location. The remaining signals down the length of the pipe are much less in amplitude.

The auto-positioning system pipe scan data for 10 sequential tests with the transducers set up in a v-bounce configuration was also plotted with signal strength in volts as a function of distance in inches. The scan was set for the full length of the positioning assembly to allow analysis of the received signal for the length of potential scan. The auto-positioning system scanned the pipe with the movable transceiver and the received signal was transferred to and recorded by the user interface program.

The auto-positioning system pipe scan data for 10 sequential tests with the system set up to measure the w-bounce signal was plotted with signal strength in volts as a function of distance in inches. The scan was set for the proximity of expected optimum receiver signal. The auto-positioning system scanned the pipe with the movable transceiver and the received signal was transferred to and recorded by the user interface program.

Analysis of the auto-positioning repeatability test for a w-bounce waveform response shows a longer range (distance) with a higher output than the v-bounce. In the v-bounce analysis, the waveform held its peak voltage values for approximately 1.27 cm (0.5 in), while the w-bounce held its highest voltages for around 2.54 to 3.81 cm (1 to 1.5 in) on average.

Using the positioning system requires extensive user-input parameters yielding less setup time compared to other systems. Testing indicated that the position of a receiver is critical for detecting an acceptable wave from the transmitter. The positioning system correlated well to the flow meters and the analytical calculations, with a range of initial test error of less than 5 percent. This implies that the positioning system results are reasonably close to the values obtained through two other flowmeter software and separate analytical calculations. This is not to assert that the positioning system exhibits any more absolute error than the other methods of transducer distance determination. The implication is that the positioning system is within the range of reasonable accuracy. It should be noted that any of the singular methods could be the most accurate method of distance determination, including the positioning system.

All of the methods and apparatus disclosed herein can be made and executed without undue experimentation in light of the present disclosure. While the methods of this invention have been described in terms of specific embodiments, it will be apparent to those of skill in the art that variations may be applied to the methods and apparatus and in the steps or in the sequence of steps of the methods described herein without departing from the concept, spirit and scope of the invention. All such similar substitutes and modifications apparent to those skilled in the art are deemed to be within the spirit, scope and concept of the invention as defined by the following claims.

What is claimed is:

1. An ultrasonic transducer apparatus for determining the optimal transducer position for flow measurement along a conduit outer surface, comprising:
    a transmitting transducer for transmitting an ultrasonic signal, said transducer affixed to a conduit outer surface;
    a guide rail attached to a receiving transducer for guiding movement of a receiving transducer along the conduit outer surface, wherein the receiving transducer receives an ultrasonic signal from the transmitting transducer and sends a signal to a data acquisition system; and
    a motor for moving the receiving transducer along the guide rail, wherein the motor is controlled by a controller.

2. The apparatus of claim 1, further comprising an encoder for determining a location of the receiving transducer.

3. The apparatus of claim 2, wherein the encoder is located remotely from the motor.

4. The apparatus of claim 2, wherein the encoder comprises a software program to track the location of the receiving transducer.

5. The apparatus of claim 1, further comprising an ultrasonic flowmeter that comprises the transmitting transducer and the receiving transducer to provide excitation signal for the transmitting transducer and for processing of an output signal from the receiving transducer.

6. The apparatus of claim 1, further comprising a programmable data acquisition and control system with digital and analog inputs/outputs for collecting output signal strength from transmitting and receiving transducers, creating a signal strength data file, searching of said data file for a user-defined parameter, and directing said motor to move the receiving transducer to a desired location along the conduit.

7. The apparatus of claim 6, wherein the data acquisition and control system comprises a user interface program for parameter input.

8. The apparatus of claim 1, wherein the transmitting transducer comprises a piezo electric material.

9. The apparatus of claim 1, wherein the receiving transducer comprises a piezo electric material.

10. The apparatus of claim 1, wherein the receiving transducer moves linearly along the conduit outer surface.

11. The apparatus of claim 1, wherein the receiving transducer moves linearly along the conduit outer surface parallel to that of the transmitting transducer.

12. The apparatus of claim 1, further comprising a shock absorber system to allow the receiving transducer to make continuous contact with the conduit outer surface.

13. A method for determining the optimum flow measurement receiving transducer position along a conduit outer surface, comprising:
    a) affixing a transmitting transducer to a conduit outer surface;
    b) moving a receiving transducer on the conduit outer surface, wherein the receiving transducer is moved along a guide rail by a motor;
    c) transmitting an ultrasonic signal from the transmitting transducer that is received by the receiving transducer;
    d) communicating the signal received by the receiving transducer to a data acquisition and control system; and
    e) repeating steps b) through d) along a length of the conduit outer surface.

14. The method of claim 13, further comprising creating a data file of the signals received by the receiving transducer.

15. The method of claim 14, further comprising searching the data file for an optimum value of a parameter.

16. The method of claim 15, further comprising calculating an optimum receiving transducer location based the optimum value of a parameter.

17. The method of claim 16, further comprising positioning the receiving transducer to the optimum receiving transducer location.

18. The method of claim 17, further comprising using the data acquisition and control system to calculate the optimum receiving transducer location and to control the positioning the receiving transducer.

19. The method of claim 18, wherein the parameter to be optimized is a wave amplitude.

20. The method of claim 13, wherein the ultrasonic signal is communicated to the data acquisition and control system from at least 10 locations along the length of the conduit outer surface.

* * * * *